US00PP35757P2

(12) United States Plant Patent
Scheffers

(10) Patent No.: US PP35,757 P2
(45) Date of Patent: Apr. 16, 2024

(54) ***DRACAENA* PLANT NAMED 'DRAWHISPI'**

(50) Latin Name: *Dracaena fragrans*
Varietal Denomination: DRAWHISPI

(71) Applicant: Dragontree Beheer B.V., Honselersdijk (NL)

(72) Inventor: Ruud Scheffers, Honselersdijk (NL)

(73) Assignee: Dragontree Beheer B.V., Honselersdijk (NL)

( * ) Notice: Subject to any disclaimer, the term of this patent is extended or adjusted under 35 U.S.C. 154(b) by 0 days.

(21) Appl. No.: 17/803,794

(22) Filed: Nov. 28, 2022

(51) Int. Cl.
*A01H 5/12* (2018.01)
*A01H 6/12* (2018.01)

(52) U.S. Cl.
USPC ..... Plt./383

(58) Field of Classification Search
USPC ..... Plt./383
See application file for complete search history.

(56) References Cited

U.S. PATENT DOCUMENTS

PP13,708 P3 * 4/2003 Scheffers ..... A01H 6/12 Plt./383
PP13,755 P3 * 4/2003 Scheffers ..... A01H 6/12 Plt./383

* cited by examiner

*Primary Examiner* — Susan McCormick Ewoldt
*Assistant Examiner* — Zachariah Allan Kay
(74) *Attorney, Agent, or Firm* — Samuel R. McCoy, Jr.

(57) ABSTRACT

A new and distinct *Dracaena* plant named 'DRAWHISPI' which is characterized by thick, durable foliage that is held nearly vertical on a short, unbranched stem, green foliage that is blotched and axially striped with greyed-green and white, foliage that is broadly, axially striped with white along the marginal zones of the foliage, and the stability of these characteristics from generation to generation.

2 Drawing Sheets

Latin name of the genus and species: The Latin name of the genus and species of the novel variety disclosed herein is *Dracaena fragrans.*

Variety denomination: The inventive cultivar of *Dracaena* disclosed herein has been given the variety denomination 'DRAWHISPI'.

BACKGROUND OF THE INVENTION

Parentage: 'DRAWHISPI' is a spontaneous branch-plant mutation of a *Dracaena fragrans* 'White Jewel' plant (U.S. Plant Pat. No. 12,433) which was discovered at a commercial greenhouse in Honselersdijk, the Netherlands in May of 2010. The mutation was initially noted for its abundance of upright, variegated foliage. Said mutation was isolated for further evaluation to confirm the uniformity and stability of the unique characteristics first observed. Upon confirmation of the stability and uniformity of the characteristics, the new plant was selected for commercialization.

Asexual Reproduction: Asexual reproduction of 'DRAWHISPI' is accomplished by way of rooting stem cuttings. Propagation was first performed in May of 2010 at the inventor's commercial greenhouse in Honselersdijk, the Netherlands. Through five subsequent generations, the unique features of this cultivar have proven to be stable and true to type.

SUMMARY OF THE. INVENTION

The cultivar 'DRAWHISPI' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'DRAWHISPI'. These characteristics in combination distinguish 'DRAWHISPI' as a new and distinct *Dracaena fragrans* cultivar:

1. *Dracaena* 'DRAWHISPI' exhibits foliage that is held nearly vertical on a short, unbranched stem; and
2. *Dracaena* 'DRAWHISPI' exhibits thick, durable foliage with a smooth laminar surface; and
3. *Dracaena* 'DRAWHISPI' exhibits green foliage that is blotched and axially striped with greyed-green and white; and
4. *Dracaena* 'DRAWHISPI' exhibits foliage that is broadly, axially striped with white along the marginal zones of the foliage.

BOTANICAL DESCRIPTION OF THE PLANT

Figure 1:
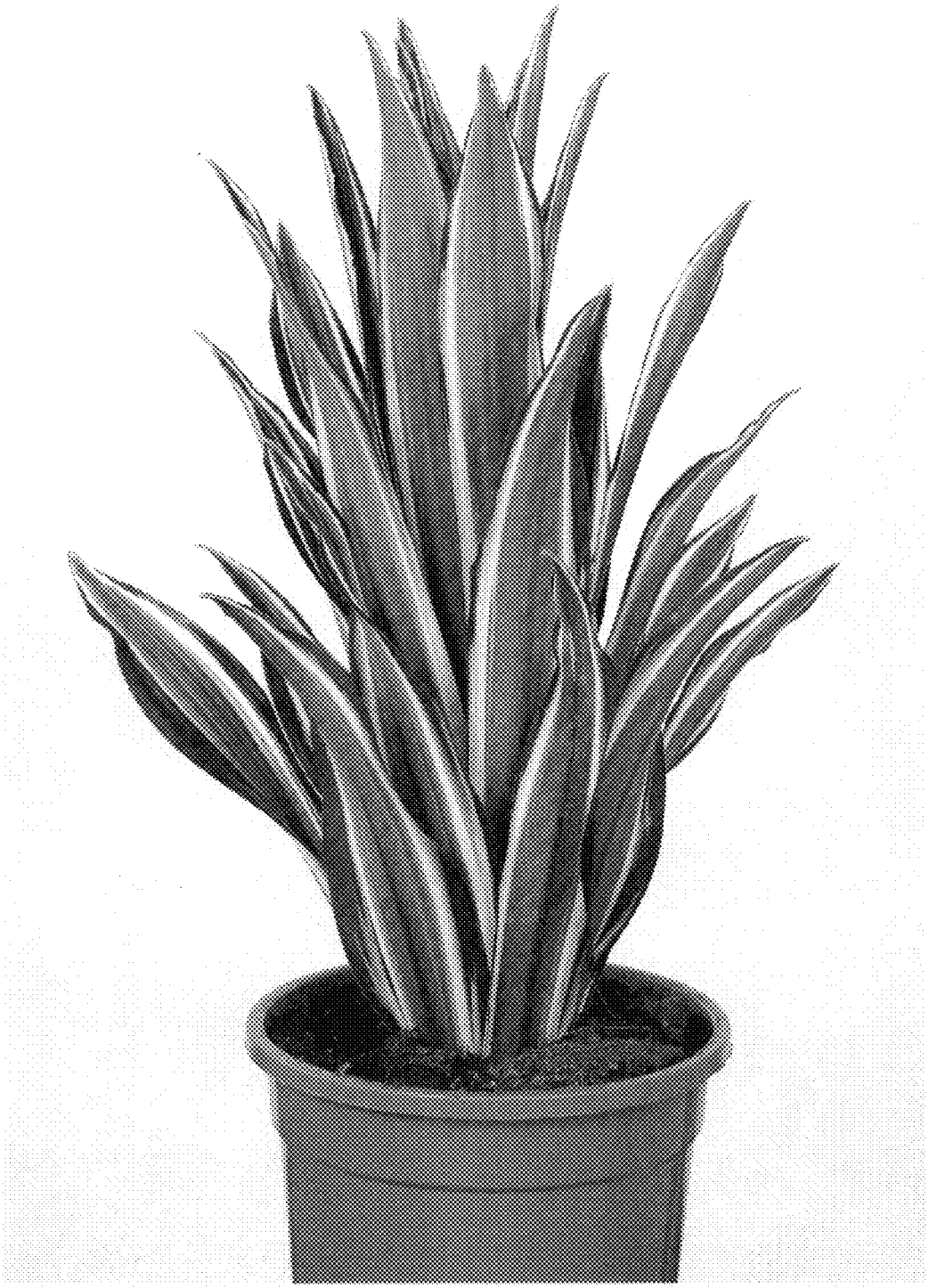
FIG. 1 illustrates, as nearly true as it is reasonably possible to make the same in color photographs of this type, an exemplary plant of 'DRAWHISPI' grown in Honselersdijk, the Netherlands. This plant, grown in a 15 cm nursery container, is approximately 12 weeks old from a rooted young plant.
Figure 2:
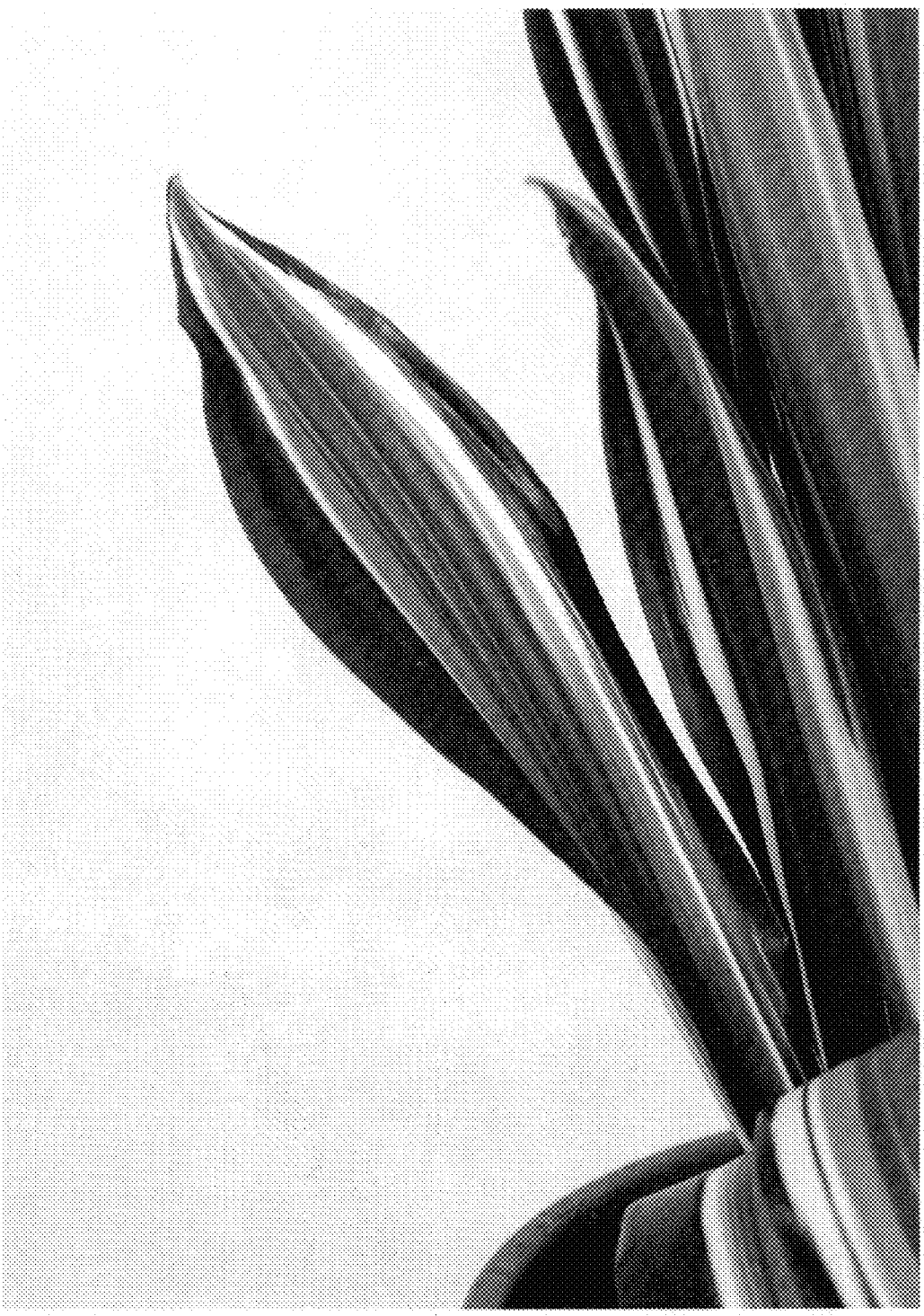
FIG. 2 illustrates, as nearly true as it is reasonably possible to make the same in color photographs of this type, the typical foliage of 'DRAWHISPI'.

The following observations and measurements, made in July of 2022, describe averages from a sample set of six specimens of 12-week-old 'DRAWHISPI' plants grown in 15 cm nursery pots in San Jose, Costa Rica. Plants were produced using conventional greenhouse production protocols for *Dracaena* sp. which consisted of growing under shade cloth, regular overhead irrigation, and chemical control of thrips insects. No photoperiodic treatments or artificial light was given to the plants.

Those skilled in the art will appreciate that certain characteristics will vary with older or, conversely, with younger plants. 'DRAWHISPI' has not been observed under all possible environmental conditions. Where dimensions, sizes, colors and other characteristics are given, it is to be understood that such characteristics are approximations or averages set forth as accurately as practicable. The phenotype of the variety may differ from the descriptions set forth herein with variations in environmental, climatic and cultural conditions. Color notations are based on *The Royal Horticultural Society Colour Chart*, The Royal Horticultural Society, London, 2015 (sixth edition).

A botanical description of 'DRAWHISPI' and comparisons with the parent plant and most similar commercial *Dracaena* cultivar known to the inventor are provided below.

Plant description:

*Growth habit*.—Compact, upright evergreen perennial with foliage born on a solitary short, unbranched stem.

*Plant profile*.—Ovate.

*Average height from base to top of foliage*.—36.1 cm.

*Average width*.—Average of 30.3 cm.

*Growth rate*.—Moderately fast growing.

*Plant vigor*.—Moderately vigorous.

*Propagation details*.—Asexual propagation is accomplished by stem cuttings.

*Time to initiate roots*.—Approximately 5 weeks are required to initiate roots at 20 degrees Celsius.

*Time to produce a marketable* 12 *cm potted plant*.—Approximately 10 weeks. Pinching will increase lateral branching.

*Disease and pest resistance or susceptibility*.—Neither tolerance nor resistance to normal diseases and pests of *Dracaena fragrans* have been observed.

*Environmental tolerances*.—Adapt to USDA Hardiness Zones 10 through 12 and temperatures as high as 40 degrees Celsius; moderate tolerance to rain and wind.

Root system:

*General*.—Fibrous; freely branched and moderately dense rooting.

*Distribution in the soil profile*.—Shallow to moderately deep.

*Texture*.—Smooth; glabrous.

Stems:

*Branching characteristics*.—Not freely branched in nature; develops lateral branches only when manipulated by man by way of pruning. Naturally produces one main stem arising from the plant's base.

*Attitude*.—Near vertical.

*Strength*.—Very strong.

*Length*.—5.0 cm.

*Diameter*.—Average 2.0 cm.

*Internode length*.—Average 1.6 cm.

*Stem texture*.—Glabrous; smooth.

*Stem luster*.—Slightly glossy.

*Color, developing stems*.—Yellow-green, nearest to RHS 145B.

*Color, mature stems*.—Yellow-green, nearest to a mixture of RHS 137B and 145A.

*Color at the internodes*.—Green, nearest to RHS 137B.

Foliage:

*Arrangement*.—Alternate.

*Attachment*.—Sheathed.

*Division*.—Simple.

*Attitude*.—Near upright.

*Number of leaves per lateral branch*.—31.

*Lamina*.—Dimensions — 23.6 cm long and 4.7 cm wide, on average. Shape — Lorate. Aspect — Slightly spiraled, with the distalmost portion on the lamina pointing downward at an average angle of minus-40 degrees to the rest of the lamina. Apex — Acute with a short, soft but pointed tip. Base — Sheathed. Sheath — Length — 2.7 cm. Width — 2.1 cm. Color, adaxial surface — Greyed-green, nearest to RHS 193A, and broadly margined white, nearest to RHS NN155C. Color, abaxial surface — Green, nearest to a mixture of RHS NN137A and NN137B, and broadly margined white, nearest to RHS NN155B. Margin — Entire; coarse undulation. Texture and luster of adaxial surface — Smooth, glabrous and moderately glossy. Texture and luster of abaxial surface — Smooth, glabrous and slightly glossy. Color — Juvenile foliage, adaxial surface — Yellow-green, nearest to RHS 144A; axially blotched and striped with both greyed-green and white, nearest to RHS N189C and NN155B; broadly, axially striped with white along the marginal zones of the foliage, nearest to RHS NN155A. Juvenile foliage, abaxial surface — Green, nearest to RHS 138B; axially blotched and striped with both greyed-green, nearest to a combination of RHS 191A; broadly, axially striped with white along the marginal zones of the foliage, nearest to RHS NN155A. Mature foliage, adaxial surface — Green, nearest to RHS 138A; axially blotched and striped with green, greyed-green and white, nearest to a combination of RHS 137A, 137B, N189D, 190B, 190C, 191C, and NN155A; broadly, axially striped with white along the marginal zones of the foliage, nearest to a mixture of RHS 155B and NN155A; margined green, nearest to a mixture of RHS NN137A and 139A. Mature foliage, abaxial surface — Green, nearest to RHS 138B; axially blotched and striped with both greyed-green and white, nearest to a combination of RHS 188A, 188B, 190B, and NN155B; broadly, axially striped with white along the marginal zones of the foliage, nearest to a mixture of RHS 155B and NN155A; margined green, nearest to RHS 137A. Venation — Pattern — Parallel. Color, adaxial surface — The main vein yellow-green, nearest to RHS 147B. All other veins are indistinguishable from the surrounding foliage. Color, abaxial surface — The main vein is green, nearest to RHS 137A. All other veins are indistinguishable from the surrounding foliage.

Inflorescence: To date, flowering has not been observed.

Flower buds: To date, flowering has not been observed.

Flower: To date, flowering has not been observed.

Reproductive organs: To date, flowering has not been observed.

Seed and fruit: To date, flowering has not been observed.

COMPARISONS WITH THE PARENT PLANT

Plants of the new cultivar 'DRAWHISPI' may be distinguished from its parent, *Dracaena fragrans* 'White Jewel' plant (U.S. Plant Pat. No. 12,433), by the characteristics described in Table 1.

TABLE 1

| Characteristic | 'DRAWHISPI' | 'White Jewel' |
|---|---|---|
| Foliage thickness. | Thicker than 'White Jewel'. | Thinner than 'DRAWHISPI'. |
| Foliage durability | More durable than 'White Jewel'. | Less durable than 'DRAWHISPI'. |
| Foliage shape. | Lorate with an acute apex which is more pointed than 'White Jewel'. | Broadly lorate, with an acute apex that is more rounded than 'DRAWHISPI'. |
| Foliage attitude. | Upright; near vertical. | Relaxed. |

Plants of the new cultivar 'DRAWHISPI' are similar to the closest known commercial comparator, *Dracaena fragrans* 'Pequeria' (U.S. Plant Pat. No. 24,796), in that both plants have an upright foliage attitude. However, the two plants may be distinguished from one another by the characteristics described in Table 2.

TABLE 2

| Characteristic | 'DRAWHISPI' | 'Pequeña'. |
|---|---|---|
| Plant size. | Larger than 'Pequeña'. | Smaller than 'DRAWHISPI'. |
| Foliage size. | Larger than 'Pequeña'. | Smaller than 'DRAWHISPI'. |
| Presence of foliage variegation. | Present. | Not present. |

That which is claimed is:

1. A new and distinct cultivar of *Dracaena* plant named 'DRAWHISPI', substantially as described and illustrated herein.

* * * * *